United States Patent [19]

Schumacher et al.

[11] 4,407,729

[45] Oct. 4, 1983

[54] CATALYSTS

[75] Inventors: Ignatius Schumacher, Ballwin; Kang-Bo Wang, Creve Coeur, both of Mo.

[73] Assignee: Monsanto Company, St. Louis, Mo.

[21] Appl. No.: 313,519

[22] Filed: Oct. 21, 1981

[51] Int. Cl.³ .................. B01J 21/04; B01J 27/02; B01J 27/24

[52] U.S. Cl. .................. 502/200; 502/216; 502/219; 502/220; 502/221; 502/222

[58] Field of Search .................. 252/436, 455 Z, 439, 252/438, 462, 465

[56] References Cited

U.S. PATENT DOCUMENTS

| | | | |
|---|---|---|---|
| 2,109,873 | 3/1931 | Wilhelm | 260/142 |
| 2,256,615 | 9/1941 | Hederhort | 252/436 X |
| 2,434,833 | 1/1948 | Ciapetta | 252/436 X |
| 2,805,207 | 9/1957 | Metzger | 252/476 |
| 2,831,870 | 4/1958 | McClements et al. | 260/348.5 |
| 3,158,578 | 11/1964 | Pons, Jr. et al. | 252/436 |
| 3,208,953 | 9/1965 | Klass et al. | 252/436 X |
| 3,385,797 | 5/1968 | Bloch et al. | 252/436 X |
| 3,418,256 | 12/1968 | Rigney et al. | 252/455 Z |
| 3,793,231 | 2/1974 | Bergmann et al. | 252/463 |
| 3,962,136 | 6/1976 | Nielsen et al. | 251/454 |
| 3,966,830 | 6/1976 | Shimada et al. | 260/646 |
| 4,107,220 | 8/1978 | Owsley et al. | 260/464 |
| 4,112,006 | 9/1978 | Schubert et al. | 260/645 |

OTHER PUBLICATIONS

Hattori et al., Journal of Catalysis, vol. 68 (1981), pp. 132-143.
Hino et al., JCS Chemical Communications (1980), pp. 851-852.
Olah et al., Journal of Catalysis, vol. 61 (1980), pp. 96-102.
Olah et al., Journal of Organic Chemistry, vol. 43 (1978), pp. 4628-4630.
Olah et al., Journal of Organic Chemistry, vol. 42 (1977), pp. 4187-4191.
Harper et al., ACS Symposium on Recent Advances in Alkylation Chemistry, New Orleans, Louisiana, Mar. 20-25 (1979).
McKee et al., Industrial and Engineering Chemistry, vol. 28 (1958), pp. 662-667.

Primary Examiner—Carl F. Dees
Attorney, Agent, or Firm—W. W. Brooks; J. C. Logomasini; A. H. Cole

[57] ABSTRACT

Catalyst compositions are prepared by contacting an alumina-silica-metal oxide combination represented by the formula:

$$(Al_2O_3)_a(SiO_2)_b(M_{2/n}O)_c$$

wherein M is a metal cation selected from the group consisting of the lanthanides of rare earths, Groups 1b, 2b, 5b, 6b, 7b, and 8 of the Periodic Table of the Elements, and mixtures thereof, and a, b, and c represent weight percent of the $Al_2O_3$, $SiO_2$, $M_{2/n}O$ components, respectively, in the alumina-silica-metal oxide combination, with a being 0 to 100, b being 0 to 100, and c being 0 to 50, and n represents an integer from 1 to 7 of the valence of the metal cation, with the proviso that the sum of a+b must be greater than 0, with a catalytically effective amount of sulfur trioxide.

25 Claims, No Drawings

CATALYSTS

CROSS-REFERENCE TO RELATED APPLICATION

"Vapor Phase Nitration of Aromatic Compound", Ser. No. 313,522, filed Oct. 21, 1981.

BACKGROUND OF THE INVENTION

1. Field of the Invention

This invention relates to catalyst compositions and a process for preparing such compositions. More particularly, this invention relates to catalyst compositions comprising the adduct of:

(a) an alumina-silica-metal oxide combination represented by the formula:

$$(Al_2O_3)_a(SiO_2)_b(M_{2/n}O)_c$$

wherein M is a metal cation selected from the group consisting of the lanthanides or rare earths, Groups 1b, 2b, 5b, 6b, 7b, and 8 of the Periodic Table of the Elements, and mixtures thereof, and a, b, and c represent weight percent of the $Al_2O_3$, $SiO_2$, and $M_{2/n}O$ components, respectively, in the alumina-silica-metal oxide combination, with a being 0 to 100, b being 0 to 100, and c being 0 to 50 and n represents an integer from 1 to 7 of the valence of the metal cation, with the proviso that the sum of (a+b) must be greater than 0, and (b) a catalytically effective amount of sulfur trioxide.

The catalyst compositions of this invention may be used for any of a wide variety of purposes generally known in the art. Thus, for example, the compositions are useful as catalysts in the transformation of numerous organic compounds in the vapor phase such as alkylation and/or nitration of aromatic compounds, dehydrogenation reactions, oxidation reactions, hydrogenation reactions, skeletal isomerization reactions, and the like. The catalyst compositions may be employed in a manner identical to that for catalysts heretofore known in the art for such transformations.

2. Description of the Prior Art

Various vapor phase processes which employ numerous catalyst compositions are known for the transformation of organic compounds. Thus, the vapor phase nitration of benzene and toluene in the present of silica gel at temperatures ranging from about 275° C. to about 310° C. is described in McKee and Wilhelm, *Industrial and Engineering Chemistry*, 28(6), 662–667 (1936) and U.S. Pat. No. 2,109,873. Bauxite and alumina were reported to be ineffective as catalysts in the vapor phase nitration of benzene.

U.S. Pat. No. 4,107,220 discloses the use of molecular sieves (aluminosilicates) having a pore size varying from about 5 Å to about 10 Å as catalysts to control the para-to-ortho isomer distribution of nitrochlorobenzene in the vapor phase nitration of chlorobenzene. Suitable temperatures are reported to range from about 190° C. to about 290° C.

The use of silver-containing catalysts in processes for the direct oxidation of ethylene to ethylene oxide is disclosed in numerous patents, for example, U.S. Pat. Nos. 3,962,136, 3,793,231, 2,831,870 to cite just a few.

Crystalline alumina silicate is reported in Harper et al, "Alkylation of Benzene with Propylene over a Crystalline Alumina Silicate," *ACS Symposium on Recent Advances in Alkylation Chemistry*, New Orleans, LA, Mar. 20–25 (1979) to be an effective catalyst in the alkylation of benzene with propylene to produce cumene and minor amounts of poly-isopropylbenzenes.

The vapor phase Friedel-Crafts alkylation of toluene and phenol with alkyl chloroformates and alkyl oxalates in the presence of a solid superacid, perfluorinated resinsulfonic acid, known as Nafion ® -H, as catalyst is described in Olah et al, *Journal of Catalysis*, 61(1), 96–102 (1980). Such solid acids are designated as solid superacids due to their high acid strength, that is, having an acid strength stronger than 100 percent sulfuric acid. Similar alkylations of benzene with ethylene and propylene are disclosed in Olah et al, *Journal of Organic Chemistry*, 42(26), 4187–4191 (1977).

Solid superacids also are disclosed as effective to catalyze the skeletal isomerization of butane to isobutane and minor amounts of by-products. Among the solid superacids disclosed are zirconia/sulfate ion [Hino et al, *JCS Chemical Communications*, 851–852 (1980)], titania/sulfate ion [*Idem, ibid* 1148–1149 (1979)], iron (III) oxide/sulfate ion [Hino et al, *Chemistry Letters* (Japan) 1259–1260 (1979)], and $SbF_5$—$TiO_2$—$SiO_2$, $SbF_5$—$TiO_2$, and $SbF_5$—$SiO_2$—$Al_2O_3$ [Tanabe et al, *Chemistry Letters* (Japan), 625–626 (1979)].

Although these prior art catalysts are effective to provide the desired product, the commercial utility of a catalyst system is highly dependent upon the cost of the system, the conversion of the reactant(s) and the yield of the desired product(s). In many cases, a reduction in the cost of a catalyst system on the order of a few cents per pound or a small percent increase in the yield of the desired product represents a tremendous commercial economical savings. Accordingly, research efforts are continually being made to define new or improved catalyst systems and methods and processes of making new and old catalyst systems to reduce the cost and/or upgrade the activity and selectivity of such catalyst systems in particular processes. The discovery of the catalyst compositions of the present invention, therefore, is believed to be a decided advance in the catalyst art.

SUMMARY OF THE INVENTION

It is an object of this invention to provide novel catalyst compositions highly effective for the vapor phase transformation of organic compounds.

Another object of this invention is to provide novel catalyst compositions highly effective for the vapor phase nitration of aromatic compounds.

Yet another object of this invention is to provide a process for the preparation of novel catalyst compositions highly effective for the vapor phase transformation of organic compounds.

To achieve these and other objects which will become apparent from the accompanying description and claims, catalyst compositions are provided which comprise the adduct of:

(a) an alumina-silica-metal oxide combination represented by the formula:

$$(Al_2O_3)_a(SiO_2)_b(M_{2/n}O)_c$$

wherein M is a metal cation selected from the group consisting of the lanthanides or rare earths, Groups 1b, 2b, 5b, 6b, 7b, and 8 of the Periodic Table of the Elements, and mixtures thereof, and a, b, and c represent weight percent of the $Al_2O_3$, $SiO_2$, and $M_{2/n}O$ components, respectively, in the alumina-silica-metal oxide combination, with a being 0 to 100, b being 0 to 100, and c being 0 to 50, and n is an integer from 1 to 7 of the valence of the metal cation, with the proviso that the sum of (a+b) must be greater than 0, and (b) a catalytically effective amount of sulfur trioxide.

DESCRIPTION OF THE PREFERRED EMBODIMENTS

In accordance with this invention, novel catalyst compositions are provided which comprise the adduct of:

(a) an alumina-silica-metal oxide combination represented by the formula:

$$(Al_2O_3)_a(SiO_2)_b(M_{2/n}O)_c$$

wherein M is a metal cation selected from the group consisting of the lanthanides or rare earths, Groups 1b, 2b, 5b, 6b, 7b, and 8 of the Periodic Table of the Elements, and mixtures thereof, and a, b, and c represent weight percent of the $Al_2O_3$, $SiO_2$, and $M_{2/n}O$ components, respectively, in the alumina-silica-metal oxide combination, with a being 0 to 100, b being 0 to 100, and c being 0 to 50, and n represents an integer from 1 to 7 of the valence of the metal cation, with the proviso that the sum of (a+b) must be greater than 0, and (b) a catalytically effective amount of sulfur trioxide.

Alumina-silica-metal oxide combination materials suitable for use in the present invention are those which yield the novel catalyst compositions of the present invention which are effective to catalyze the transformation of organic compounds in the vapor phase with high conversion of the reactants and high yield of desired products. Such materials may be crystalline, noncrystalline, or mixtures thereof. Nonlimiting representative examples of suitable alumina-silica-metal oxide combination materials are alumina (a=100; b=c=0), silica (b=100; a=c=0), alumina-silica, including aluminosilicates such as synthetic and naturally occurring zeolites, and mixtures thereof.

In many instances, it may be desirable to modify the physical and/or chemical properties of the alumina-silica-metal oxide combination or the spectrum of products produced in the many and varied reactions in which the compositions of the present invention are effective as catalysts. To this end, one of more metal oxide components may be incorporated into the alumina-silica-metal oxide combination. Depending upon the particular effect desired or property to be modified, suitable metal oxides are those wherein the metal cation (M) is selected from the group consisting of the lanthanides or rare earths, Groups 1b, 2b, 5b, 6b, 7b, and 8 of the Periodic Table of the Elements, and mixtures thereof. For example, adducts formed from the alumina-silica-metal oxide combinations containing oxides of vanadium, silver, copper, manganese, nickel, molybdenum, and tungsten may be employed for the production of olefin oxides from olefins. Adducts containing oxides of chromium, zinc, manganese, iron, copper, cerium, and cobalt may be employed for the production of olefinically unsaturated compounds, for example, propylene from propane, styrene from ethylbenzene, and the like. In general, metals and metal ions employed as catalysts in known prior art processes may be employed in the present invention in the same mode to effect similar reactions, but with the added advantage of enhanced activity.

The alumina-silica-metal oxide combination materials are available commercially from numerous catalyst suppliers. Such materials can also be prepared by procedures well known in the art. For example, the alumina-silica-metal oxide combination materials wherein c is greater than 0 can be prepared by known procedures for preparing supported metal oxide catalysts. The method generally employed for producing such metal oxide catalysts involves impregnating the support—alumina, silica, and alumina-silica, for example—with a soluble metal salt convertible to the metal oxide, separating the saturated solid, and heating to remove a major portion of the solvent. The resultant material is then calcined to convert the metal salt to the corresponding metal oxide. In many cases, a multiple impregnation technique is employed to achieve a higher concentration of metal oxide on the support.

Another well-known technique involves suspending the support material in a solution of a metal salt convertible to the metal oxide, completely or partially evaporating the solvent, and possibly mixing of the resultant material with an organic binder and forming structures thereof. The dried structures are then heated to an elevated temperature to effect complete removal of solvent, burning out of the organic material, and as previously noted, conversion of the metal salt to the corresponding metal oxide.

The alumina-silica-metal oxide combination material need not necessarily be completely free of impurities. Thus, materials or substances other than $Al_2O_3$, $SiO_2$, and $M_{2/n}O$ which cause little, if any, adverse effect upon the resultant catalyst's activity may be present. Impurities which are commonly associated with alumina and alumina-containing materials includes, for example, oxides of the alkali metals, the alkaline earth metals, and titanium of Group 4b of the Periodic Table of the Elements. In general, such impurities may be present in amounts not exceeding 5 weight percent.

The term Periodic Table of the Elements, as employed herein refers to the Periodic Table of the Elements published in *CRC Handbook of Chemistry and Physics*, 60th ed., Weast, Ed., CRC Press, Inc., Boca Raton, FL, 1979, Inside Front Cover.

Sulfur trioxide ($SO_3$) is an essential component of the catalyst compositions of the present invention. It is added to the alumina-silica-metal oxide combination in a catalytically effective amount. It may be charged directly as sulfur trioxide in the vapor or gaseous phase. Alternatively, it may be provided indirectly by charging to the alumina-silica-metal oxide combination a mixture of sulfur dioxide ($SO_2$) and nitrogen dioxide ($NO_2$) which react to produce sulfur trioxide and inert (for purposes of the present invention) nitric oxide (NO). When a mixture of sulfur dioxide and nitrogen dioxide is employed, a stoichiometric mole ratio of at least 1 is required. It is preferred, however, to employ an excess of sulfur dioxide, usually on the order of about 2 to 3 moles per mole of nitrogen dioxide.

In general, when providing the sulfur trioxide, the indirect method of charging a mixture of sulfur dioxide and nitrogen dioxide to the alumina-silica-metal oxide combination is preferred in that both sulfur dioxide and nitrogen dioxide, as well as nitric oxide, exist in the gaseous state at ambient temperatures (approximately 25° C.) and above while sulfur trioxide exists as a liquid at ambient temperatures and under the usual and preferred preparative conditions would first have to be converted to a vapor prior to contacting the alumina-silica-metal oxide combination.

As previously indicated, the catalyst compositions of the present invention comprise an adduct, an essential component of which is sulfur trioxide. It is recognized, of course, that when a mixture of sulfur dioxide and nitrogen dioxide is charged to the reactor to provide the sulfur trioxide, the adsorbed species may in fact be a complex or combination of sulfur trioxide and nitrogen dioxide. However, regardless of the actual composition of the adsorbed species, it is conveniently referred to herein as sulfur trioxide and is meant to encompass all such compositions, whether sulfur trioxide, sulfur trioxide-nitrogen dioxide complex, or some combination thereof, as well as unreacted mixtures of sulfur dioxide and nitrogen dioxide.

The catalyst compositions of the present invention are normally prepared by contacting the alumina-silica-metal oxide combination with sulfur trioxide (directly or indirectly as previously described) in the vapor phase under conditions conducive to the formation of the adduct and for a time sufficient to induce the desired weight gain. The amount of added sulfur trioxide (as indicated by the gain in weight) is not narrowly critical. All that is necessary is that a catalytically effective amount of sulfur trioxide be added. In general, it has been found that at least 5 weight percent, based on the weight of the alumina-silica-metal oxide combination, sulfur trioxide is required to provide the enhanced activity exhibited by the catalyst compositions of the present invention. Also, although not critical, an upper limit of about 40 weight percent, with about 10 weight percent being preferred, has been found to be desireable in that little, if any, advantage is demonstrated for higher concentrations of sulfur trioxide. Thus, both higher and lower concentrations than the stated 5 to 40 weight percent range can be employed, if desired, but since such concentrations offer no particular advantage over the stated desirable range, and may in fact affect adversely the catalyst activity, particularly at concentrations less than about 5 weight percent, the stated 5 to 40 weight percent range is desirably employed.

The conditions under which the catalyst compositions are prepared can vary widely. All that is necessary is that the sulfur trioxide, whether charged directly or indirectly, exist in the vapor phase while contacting the alumina-silica-metal oxide combination. Thus, the catalyst preparation can be conducted at temperatures ranging from ambient temperatures (about 25° C.) (when sulfur dioxide and nitrogen dioxide are employed to provide the sulfur trioxide) to about 300° C. or higher. Preferred temperatures, however, range from about 150° C. to about 250° C., with 175° C. to about 225° C. being particularly preferred. At such preferred temperatures, the uptake of sulfur trioxide is reasonably rapid with a minimum of loss of reactant gases resulting from unreacted pass-through. In general, and for convenience, the catalyst preparations can be performed at the temperature to be employed in the subsequent reaction in which the catalyst is to be employed.

The catalyst preparations are conducted under substantially anhydrous conditions. This is necessary since sulfur trioxide readily undergoes reaction with water to form sulfuric acid which, prior to formation of the adducts comprising the catalyst compositions of the present invention, may exhibit an adverse effect in subsequent reactions. As employed herein, the term "substantially anhydrous" means not more than 5 weight percent water is present in the reaction as part of the catalyst-forming components.

The catalyst compositions of the present invention are conveniently prepared in an apparatus of the type suitable for carrying out chemical reaction in the vapor phase. In this manner the catalyst preparation can be performed in the same reactor as that to be employed for the subsequent reaction or transformation of organic compounds. It can be conducted in a fixed bed, moving bed, or a fluidized bed system to effect contacting of the alumina-silica-metal oxide combination and the sulfur trioxide. And, as previously noted, catalyst preparation is preferably carried out by continually passing a vaporous mixture of sulfur dioxide and nitrogen dioxide in a 2-3/1 mole ratio over a bed of the alumina-silica-metal oxide combination under substantially anhydrous conditions at a temperature from about 25° C. to about 300° C., and usually, about 175° C. to about 225° C.

The following specific examples illustrating the best presently known method of practicing this invention are described in detail in order to facilitate a clear understanding of the invention. It should be understood, however, that the detailed expositions of the application of the invention while indicating preferred embodiments, are given by way of illustration only and are not to be construed as limiting the invention since various changes and modifications within the spirit of the invention will become apparent to those skilled in the art from this detailed description.

EXAMPLES 1–15

Preparation of Catalysts

A stainless steel tube 40.64 cm (16 inches) in length and 2.54 cm (1 inch) outside diameter, was employed as the reactor. An alumina-silica-metal oxide combination material was placed in the reactor and dried, if necessary, by heating to about 225° C. under a constant stream of dry nitrogen for about 1 hour. The temperature was set at the preparation temperature, usually 175° C., and sulfur dioxide, along with nitrogen dioxide (in a nitrogen carrier stream), unless specified otherwise, was charged to the reactor containing the alumina-silica-metal oxide combination in approximately a 2-3/1 mole ratio until the sulfur trioxide uptake had reached the desired amount. The time period was usually about 1 hour. The parameters and results are tabulated in Table 1.

TABLE 1

| ALUMINA-SILICA-METAL OXIDE COMBINATION[1] | | | | |
|---|---|---|---|---|
| (EXAMPLE) | | \multicolumn{3}{c}{$(Al_2O_3)_a(SiO_2)_b(M_{2/n}O)_c$} |
| CATALYST | Name[2] | a | b | c |
| | | \multicolumn{3}{c}{Wt %} |
| 1 | Boehmite[8] | 100 | 0 | 0 |
| 1a[9] | " | " | " | " |
| 2 | Zeolon 900H[8] | 9.4 | 90.6 | " |
| 2a[10] | " | " | " | " |
| 2b[11] | " | " | " | " |
| 3 | Silica-alumina[12] | 12 | 87 | " |
| 3a[13] | " | " | " | " |
| 3b[14] | " | " | " | " |
| 4 | " | " | " | " |
| 5[15] | Silica-alumina[16] | 50 | 50 | " |
| 5a[17] | " | " | " | " |
| 6 | Silica[18] | 0 | 100 | " |
| 7 | Silica gel[19] | " | " | " |
| 8[20] | Cobalt oxide-molybdenum oxide on alumina[16] | 86.5 | 0 | 13.5[21] |
| 8a[22] | Cobalt oxide-molybdenum oxide on alumina[16] | " | " | " |
| 9[23] | Cobalt oxide-molybdenum oxide on alumina[16] | 80.5 | " | 19.5[24] |

TABLE 1-continued

ALUMINA-SILICA-METAL OXIDE COMBINATION[1]

| | | | | |
|---|---|---|---|---|
| 10[25] | Silica-alumina[26] | 45 | 53 | 0 |
| 10a[27] | " | " | " | " |
| 10b[28] | " | " | " | " |
| 10c[29] | " | " | " | " |
| 11[30] | Nickel oxide-tungsten oxide on silica-alumina[12] | 17.4 | 65 | 17.6[31] |
| 12[32] | Cobalt oxide on silica (α-quartz)[16] | 0 | 83.7 | 16.3[33] |
| 13[33] | Alumina[8] | 100 | 0 | 0 |
| 14 | Silica-alumina[12] | 12 | 87 | " |
| 15 | " | " | " | " |
| 11[30] | | 5.2, 5.1 | 128.0 | 41.0 | " | 1.0 | " |
| 12[32] | | 12.5, 14.6 | 150.0 | 60.0 | " | " | " |
| 13[33] | | 11.2, 12.1 | 53.5 | 54.0 | 21.3 | 2.0 | " |
| 14 | | 19.6, 22.5 | 126.0 | 55.0 | 31.0 | 2.5 | " |
| 15 | | 20.5, 22.5 | " | " | " | 2.2 | " |

| (EXAMPLE) CATALYST | Physical Properties | | | Amount, g | |
|---|---|---|---|---|---|
| | Surface Area m²/g | Form Size, cm. | Shape | Initial[3] | Final[4] |
| 1 | 292.2 | 0.32 × 0.32 | Pellets | 112.9 | 103.6 |
| 1a[9] | " | " | " | " | " |
| 2 | 400-450 | " | " | 98.9 | 86.1 |
| 2a[10] | " | " | " | " | " |
| 2b[11] | " | " | " | " | " |
| 3 | 425-450 | " | " | 84.7 | 83.1 |
| 3a[13] | " | " | " | " | " |
| 3b[14] | " | " | " | " | " |
| 4 | " | " | " | 83.6 | 80.4 |
| 5[15] | 260 | 0.64 × 0.64 | Tablets | — | 105.5 |
| 5a[17] | " | " | " | " | " |
| 6 | 350 | 0.14-0.48 | Spheres | " | 54.8 |
| 7 | — | 0.12-0.34 | Crystallite | 92.4 | 90.4 |
| 8[20] | " | 0.32 × 0.32 | Pellets | — | 100.4 |
| 8a[22] | " | " | " | " | " |
| 9[23] | " | 0.34-0.48 | Spheres | " | 125.2 |
| 10[25] | " | 0.38 × 0.38 | Pellets | " | 120.1 |
| 10a[27] | " | " | " | " | " |
| 10b[28] | " | " | " | " | " |
| 10c[29] | " | " | " | " | " |
| 11[30] | 230 | 0.21 × 0.21 | " | " | 101.0 |
| 12[32] | 110 | 0.40-0.64 | Spheres | " | " |
| 13[33] | 306 | 0.32 | " | " | 92.8 |
| 14 | 425-450 | 0.32 × 0.32 | Pellets | " | 87.0 |
| 15 | " | " | " | " | 91.3 |

CATALYST PREPARATION CONDITIONS

| (EXAMPLE) CATALYST | SULFUR TRIOXIDE UPTAKE g, wt. %[5] (Totals)[6] | Flow Rate ml/min. | | | Time Hours | Temp. °C. |
|---|---|---|---|---|---|---|
| | | Sulfur Dioxide | Nitrogen Dioxide | Carrier Gas[7] | | |
| 1 | 12.5, 12.1 | 107.0 | 49.0 | 31.0 | 1.0 | 175 |
| 1a[9] | 8.9, 8.6 (21.4, 20.6) | 129.0 | 154.0 | " | " | " |
| 2 | 9.1, 10.6 | 107.6 | 53.6 | " | " | " |
| 2a[10] | 5.2, 6.0 (14.3, 16.6) | 108.0 | 54.0 | " | " | " |
| 2b[11] | 1.1, 1.3 (15.4, 17.9) | " | " | " | " | " |
| 3 | 7.9, 9.5 | 107.0 | " | " | " | " |
| 3a | 11.8, 14.2 (19.7, 23.7) | " | 60.0 | " | " | " |
| 3b | 10.1, 12.2 (29.8, 35.9) | " | " | 26.3 | " | " |
| 4 | 32.2, 40.0 | " | 62.9 | 30.0 | 3.0 | 180 |
| 5[15] | 10.6, 10.0 | " | 48.8 | 31.0 | 1.0 | 175 |
| 5a[17] | 11.6, 11.0 (22.2, 21.0) | " | " | " | " | " |
| 6 | 11.5, 21.0 | " | " | " | 1.5 | " |
| 7 | 12.3, 13.6 | " | 60.0 | " | 1.0 | " |
| 8[20] | 5.8, 5.8 | 141.0 | 62.0 | " | 0.5 | " |
| 8a[22] | 4.7, 4.7 (10.5, 10.5) | 131.0 | 56.0 | " | " | " |
| 9[23] | 8.4, 6.7 | " | 46.0 | " | 1.0 | " |
| 10[25] | 6.1, 5.1 | 142.0 | 67.4 | " | 0.5 | " |
| 10a[27] | 2.7, 2.2 (8.8, 7.3) | 58.0 | 30.0 | " | " | " |
| 10b[28] | 2.9, 2.4 (11.7, 9.7) | 78.0 | 36.0 | " | " | " |
| 10c[29] | 4.8, 4.0 (16.5, 13.7) | 124.0 | 59.0 | " | " | " |

[1] Composition and properties provided by commercial supplier unless otherwise noted.
[2] Material added initially to reactor.
[3] Weight in grams prior to drying, if subsequently dried.
[4] Weight in grams after drying, if dried.
[5] Based on the weight of the alumina-silica-metal oxide combination material.
[6] The total amount of sulfur trioxide taken up by the alumina-silica-metal oxide combination material as a result of a second, third, and the like addition, as applicable, of a sulfur trioxide source, usually sulfur dioxide and nitrogen dioxide, to a previously prepared adduct.
[7] Nitrogen; carrier gas for nitrogen dioxide.
[8] Available commercially from Norton Company, Akron, Ohio 44309.
[9] Catalyst 1, after use, was purged with steam at 225° C. for 1 hour, followed by dry nitrogen at 225° C. for an additional hour, and then contacted with additional sulfur dioxide and nitrogen dioxide to provide a total sulfur trioxide uptake.
[10] Catalyst 2, after two vapor phase nitration runs, was treated as described in Footnote 9.
[11] Catalyst 2a, after one vapor phase nitration run, was treated as described in Footnote 9.
[12] Available commercially from Strem Chemicals, Inc., Newburyport, Massachusetts 01950; contained 1.0% unidentified material.
[13] Catalyst 3, after two vapor phase nitration runs, was treated with additional sulfur dioxide and nitrogen dioxide for 1 hour.
[14] Catalyst 3a, after one vapor phase nitration run, was treated as described in Footnote 13.
[15] After one vapor phase nitration run, on virgin silica-alumina (catalyst precursor) for comparative purposes (Example 34), the catalyst composition of this invention was prepared.
[16] Available commercially from United Catalysts, Inc., Louisville, Kentucky 40232.
[17] Catalyst 5, after one vapor phase nitration run, was treated as described in Footnote 13.
[18] Available commercially from Air Products and Chemicals, Inc., Allentown, Pennsylvania 18105.
[19] Available commercially from Fisher Scientific Company, Fairhaven, New Jersey 07410.
[20] After one vapor phase nitration run on virgin alumina-silica-metal oxide combination material (catalyst precursor) for comparative purposes (Example 46), the catalyst composition of this invention was prepared.
[21] M represents a mixture of cobalt (n = 2; 3.5%) and molybdenum (n = 6; 10.0%) such that c is 13.5%.
[22] Catalyst 8, after one vapor phase nitration run, was treated with sulfur dioxide and nitrogen dioxide for an additional 30 minutes.
[23] After one vapor phase nitration run on virgin alumina-silica-metal oxide combination material (catalyst precursor) for comparative purposes (Example 49), the catalyst composition of this invention was prepared by treating the alumina-silica-metal oxide combination with sulfur dioxide and nitrogen dioxide for 1 hour.
[24] M represents a mixture of cobalt (n = 2, 4.5%) and molybdenum (7 = 6; 15.0%) such that c is 19.5%.
[25] After one vapor phase nitration run on virgin alumina-silica-metal oxide combination material (catalyst precursor) for comparative purposes (Example 51), the catalyst composition of this invention was prepared.
[26] Available commercially from Ventron Corporation, Alfa Products, Danvers, Massachusetts 01923; contained 2.0% unidentified materials.
[27] Catalyst 10, after one vapor phase nitration run, was treated with additional sulfur dioxide and nitrogen dioxide.
[28] Catalyst 10a, after one vapor phase nitration run, was treated with additional sulfur dioxide and nitrogen dioxide.
[29] Catalyst 10b, after one vapor phase nitration run, was treated with additional sulfur dioxide and nitrogen dioxide.
[30] After one vapor phase nitration run on virgin alumina-silica-metal oxide combination material (catalyst precursor) for comparative purposes (Example 56), the catalyst composition was prepared.
[31] M represents a mixture of nickel (n = 2; 3.3%) and tungsten (n = 6; 14.3%) such that c is 17.6%. Composition determined by semiquantitative x-ray fluorescence.
[32] After one vapor phase nitration run on virgin alumina-silica-metal oxide combination material (catalyst precursor) for comparative purposes (Example 58), the catalyst composition was prepared.
[33] M represents cobalt (n = 2 and 3; 16.3%).

EXAMPLES 16-74

Use of Catalysts

Using the reactor system described in Examples 1-5 for preparation of the catalyst, a number of vapor phase nitration of aromatic compounds reactions were run to show the effectiveness of the catalyst compositions of the present invention as catalysts in the transformation of organic compounds.

A stream of aromatic compound was preheated and charged to the reactor tube in a humidified or water-containing stream of air. The nitrating agent, nitrogen dioxide unless otherwise specified, in a nitrogen carrier stream was mixed with the aromatic compound/air stream shortly before contact with the heated catalyst. The products were collected in a series of three chilled containers, the first of which was chilled in an ice water bath and the second and third of which were chilled in dry ice baths. Analyses were performed by gas chromatography on a Varian Associates Model 3700 instrument using a 1.83-meter (6-ft.) by 0.32-cm. (0.125-inch) outside diameter column, packed with 0.5 weight percent phosphoric acid on 5/95 weight percent SP-1000/Chromoscorb G [carboxylic acid terminated poly(ethylene nitroterephthalate) from poly(ethylene glycol), M.W., 20,000, and nitroterephthalic acid, Supelco, Inc., Bellefonte, PA 16823/diatomaceous earth, Johns-Manville Products Corp., Manville, NJ 08835] and programmed from 90° C. to 210° C. at a program rate of 10° C./min. The parameters and results are tabulated in Table 2.

TABLE 2

| EXAMPLE | CATALYST NUMBER | R | Flow Rate ml/min. | g, moles | Conc. vol. % | Temp. °C. | Carrier Gas[3] Flow Rate ml/min. |
|---|---|---|---|---|---|---|---|
| | | AROMATIC COMPOUND, R—$C_6H_5$ | | | | | |
| 16 | 1 | Cl | 22.38 | 27.0, 0.24 | 3.1 | 80 | 500.0 |
| 17 | 1a | " | 24.83 | 29.9, 0.27 | 3.4 | " | " |
| 18 | 2 | " | 27.40 | 41.3, 0.37 | 3.7 | " | " |
| 19 | 2a | " | 30.27 | 31.9, 0.28 | 4.2 | " | " |
| 20 | 2b | " | 12.03 | 14.8, 0.13 | 1.8 | " | " |
| 21 | 3 | " | 21.80 | 23.5, 0.21 | 3.0 | " | " |
| 22 | 3 | " | 25.83 | 46.7, 0.42 | 3.5 | " | " |
| 23 | 3a | " | 30.02 | 45.2, 0.40 | 4.1 | " | " |
| 24 | 3b | " | 17.86 | 32.3, 0.29 | 2.5 | " | " |
| 25 | 4 | " | 21.88 | 36.3, 0.32 | 3.1 | 85 | " |
| 26 | 4 | " | 21.89 | 39.6, 0.35 | 3.2 | " | " |
| 27 | 4[6] | " | 20.79 | 31.3, 0.28 | 3.0 | " | " |
| 28 | 4[7] | " | 69.96 | 116.0, 1.03 | 6.4 | " | 850.0 |
| 29 | 4[7] | " | 40.02 | 72.4, 0.64 | 5.0 | " | 600.0 |
| 30 | 4[7] | " | 25.27 | 45.7, 0.41 | 3.6 | " | 500.0 |
| 31 | 4[8] | " | 23.71 | 35.7, 0.32 | 3.3 | " | " |
| 32 | 4[9] | H | 93.26 | 48.7, 0.62 | 10.7 | 30 | " |
| 33 | 4[10] | " | 87.97 | 36.8, 0.47 | 9.8 | " | " |
| 34 | 5-P[5] | Cl | 31.47 | 66.8, 0.59 | 4.3 | 85 | " |
| 35 | 5 | " | 31.73 | 56.9, 0.51 | 4.4 | " | " |
| 36 | 5a | " | 28.00 | 51.1, 0.45 | 3.8 | " | " |
| 37 | 5a | " | 14.93 | 31.6, 0.28 | 2.1 | " | " |
| 38 | 6 | " | 31.24 | 47.1, 0.42 | 4.3 | " | " |
| 39 | 6 | " | 29.05 | 43.8, 0.39 | 4.0 | " | " |
| 40 | 6 | " | 17.42 | 31.0, 0.28 | 2.5 | " | " |
| 41 | 7 | " | 21.92 | 33.0, 0.29 | 3.0 | 80 | " |
| 42 | 7 | " | 30.23 | 54.7, 0.49 | 4.1 | " | " |
| 43 | 7 | " | 24.87 | 52.5, 0.47 | 3.5 | " | " |
| 44 | 7 | " | 19.22 | 34.8, 0.31 | 2.8 | " | " |
| 45 | 7 | " | 23.80 | 43.0, 0.38 | 3.5 | " | " |
| 46 | 8-P[5] | " | 25.79 | 42.1, 0.38 | 3.3 | 82 | " |
| 47 | 8 | " | 24.64 | 36.9, 0.33 | 3.2 | " | " |
| 48 | 8a | " | 24.12 | 47.6, 0.42 | 3.2 | " | " |
| 49 | 9-P[5] | " | 21.89 | 38.5, 0.34 | 2.9 | " | " |
| 50 | 9 | " | 13.44 | 20.2, 0.18 | 2.7 | " | 320.0 |
| 51 | 10-P[5] | " | 23.15 | 34.7, 0.31 | 3.2 | 85 | 500.0 |
| 52 | 10 | " | 22.23 | 31.4, 0.28 | 2.9 | 82 | " |
| 53 | 10a | " | 23.02 | 41.6, 0.37 | 3.0 | " | " |
| 54 | 10b | " | 23.02 | 41.5, 0.37 | 3.0 | " | " |
| 55 | 10c | " | 21.72 | 35.8, 0.32 | 2.9 | " | " |
| 56 | 11-P[5] | " | 23.02 | 41.2, 0.37 | 3.0 | " | " |
| 57 | 11 | " | 12.69 | 18.6, 0.17 | 2.5 | " | 320.0 |
| 58 | 12-P[5] | " | 21.04 | 35.3, 0.31 | 2.7 | " | 500.0 |
| 59 | 12 | " | 23.15 | 35.1, 0.31 | 3.0 | " | " |
| 60 | 13-P[5] | " | 22.44 | 23.1, 0.21 | 3.1 | 80 | " |
| 61 | 13 | " | 19.98 | 27.1, 0.24 | 2.8 | " | " |
| 62 | 14[11] | H | 54.06 | 56.5, 0.72 | 9.4 | 21 | — |
| 63[12] | " | " | 54.60 | 57.0, 0.73 | 8.6 | " | — |
| 64 | " | " | 42.71 | 44.6, 0.57 | 7.5 | " | — |
| 65[12] | " | " | 40.92 | 42.8, 0.55 | 6.9 | " | — |
| 66 | " | " | 41.88 | 43.8, 0.56 | 7.3 | 23 | — |
| 67 | " | " | 40.27 | 42.1, 0.54 | 7.3 | 22 | — |
| 68 | " | " | 40.99 | 47.1, 0.60 | 7.2 | 18 | — |
| 69 | " | $CH_3$ | 30.99 | 35.2, 0.38 | 5.9 | 21 | — |
| 70 | " | " | 29.09 | 41.3, 0.45 | 5.6 | " | — |
| 71 | " | " | 33.45 | 41.2, 0.45 | 4.7 | " | — |
| 72 | " | " | 36.50 | 40.1, 0.44 | 5.0 | " | — |
| 73 | 15[13] | $C_2H_5O$ | 38.35 | 58.6, 0.55 | 6.7 | " | — |
| 74 | " | " | 27.38 | 44.8, 0.42 | 2.5 | " | — |

| EXAMPLE | Flow Rate ml/min. | g, moles | Conc. vol. % | Temp. °C. | Carrier Gas[4] Flow Rate ml/min. | NITRATING AGENT/AROMATIC COMPOUND molar ratio |
|---|---|---|---|---|---|---|
| | NITRATING AGENT[1] | | | | | |
| 16 | 54.66 | 26.9, 0.58 | 7.7 | 15 | 31.0 | 2.42 |

TABLE 2-continued

| | | | | | | |
|---|---|---|---|---|---|---|
| 17 | 66.23 | 32.6, 0.71 | 9.1 | " | " | 2.63 |
| 18 | 56.34 | 34.7, 0.75 | 7.8 | " | " | 2.03 |
| 19 | 61.66 | 26.6, 0.59 | 8.5 | " | " | 2.11 |
| 20 | 41.44 | 20.8, 0.45 | 6.0 | " | " | 3.46 |
| 21 | 54.29 | 24.0, 0.52 | 7.6 | " | " | 2.48 |
| 22 | 65.02 | 48.1, 1.05 | 8.8 | " | " | 2.50 |
| 23 | 60.18 | 37.1, 0.81 | 8.2 | " | " | 2.02 |
| 24 | 45.11 | 33.4, 0.73 | 6.4 | " | " | 2.52 |
| 25 | 62.92 | 42.6, 0.93 | 8.8 | " | 30.0 | 2.91 |
| 26 | 38.82 | 28.7, 0.62 | 5.7 | " | 21.0 | 1.77 |
| 27 | 26.59 | 16.4, 0.36 | 3.9 | " | 19.0 | 1.29 |
| 28 | 39.91 | 27.0, 0.59 | 3.6 | " | " | 0.57 |
| 29 | 30.43 | 22.5, 0.49 | 3.8 | " | " | 0.77 |
| 30 | 33.78 | 25.0, 0.54 | 4.8 | " | " | 1.32 |
| 31 | 41.75 | 25.7, 0.56 | 5.8 | " | 21.0 | 1.75 |
| 32 | 98.69 | 30.4, 0.66 | 11.3 | " | 47.5 | 1.06 |
| 33 | 116.34 | 28.7, 0.62 | 13.0 | " | 69.0 | 1.32 |
| 34 | 49.07 | 42.1, 0.92 | 6.8 | " | 31.0 | 1.56 |
| 35 | 49.15 | 36.3, 0.79 | 6.8 | " | " | 1.55 |
| 36 | 53.51 | 39.4, 0.86 | 7.4 | " | " | 1.91 |
| 37 | 36.27 | 31.5, 0.68 | 5.1 | " | " | 2.43 |
| 38 | 55.68 | 34.3, 0.75 | 7.6 | " | " | 1.79 |
| 39 | 51.13 | 31.5, 0.68 | 7.1 | " | " | 1.74 |
| 40 | 35.47 | 26.0, 0.57 | 5.1 | " | " | 2.04 |
| 41 | 60.63 | 37.4, 0.81 | 8.3 | " | " | 2.79 |
| 42 | 55.62 | 41.1, 0.89 | 7.6 | " | " | 1.82 |
| 43 | 48.00 | 41.4, 0.90 | 6.7 | " | " | 1.91 |
| 44 | 37.60 | 27.8, 0.60 | 5.5 | " | 21.0 | 1.94 |
| 45 | 37.01 | 27.4, 0.60 | 5.4 | " | " | 1.58 |
| 46 | 55.66 | 37.8, 0.82 | 7.2 | 12 | 31.0 | 2.16 |
| 47 | 53.76 | 33.2, 0.72 | 7.0 | " | " | 2.18 |
| 48 | 51.12 | 40.8, 0.89 | 6.7 | " | " | 2.12 |
| 49 | 48.92 | 34.8, 0.76 | 6.5 | " | " | 2.24 |
| 50 | 29.12 | 17.9, 0.39 | 5.7 | " | 24.0 | 2.17 |
| 51 | 57.49 | 35.6, 0.77 | 8.0 | " | 31.0 | 2.48 |
| 52 | 59.73 | 33.0, 0.72 | 7.8 | " | " | 2.57 |
| 53 | 52.89 | 39.3, 0.85 | 7.1 | " | " | 2.30 |
| 54 | 51.02 | 37.9, 0.82 | 6.7 | " | " | 2.22 |
| 55 | 52.27 | 35.6, 0.77 | 6.9 | " | " | 2.41 |
| 56 | 47.91 | 35.4, 0.77 | 6.3 | " | " | 2.08 |
| 57 | 25.39 | 15.8, 0.34 | 5.0 | " | 24.0 | 2.00 |
| 58 | 60.41 | 40.8, 0.89 | 7.8 | " | 31.0 | 2.87 |
| 59 | 52.27 | 32.3, 0.70 | 6.8 | " | " | 2.26 |
| 60 | 72.12 | 30.4, 0.66 | 9.9 | 15 | 30.0 | 3.14 |
| 61 | 69.80 | 38.7, 0.84 | 9.6 | " | " | 3.50 |
| 62 | 67.52 | 41.6, 0.90 | 11.7 | 10 | 29.0 | 1.25 |
| 63[12] | 97.42 | 60.0, 1.30 | 15.4 | 15 | 50.0 | 1.78 |
| 64 | 67.18 | 41.4, 0.90 | 11.8 | 10 | 29.0 | 1.58 |
| 65[12] | 85.07 | 52.4, 1.14 | 14.3 | 15 | 45.0 | 2.07 |
| 66 | 73.71 | 45.4, 0.99 | 12.9 | 10 | 29.0 | 1.77 |
| 67 | 42.97 | 26.5, 0.58 | 7.8 | " | " | 1.07 |
| 68 | 69.35 | 47.0, 1.02 | 12.2 | " | " | 1.70 |
| 69 | 48.61 | 24.0, 0.52 | 9.2 | " | " | 1.37 |
| 70 | 37.22 | 22.9, 0.50 | 7.2 | " | " | 1.11 |
| 71 | 43.58 | 26.8, 0.58 | 6.1 | " | 36.5 | 1.29 |
| 72 | 62.12 | 38.3, 0.83 | 8.5 | 15 | " | 1.89 |
| 73 | 65.98 | 37.9, 0.82 | 11.6 | 10 | " | 1.49 |
| 74 | 68.29 | 42.1, 0.92 | 6.1 | " | " | 2.19 |

| | WATER | | | | Carrier Gas[3] | REACTION CONDITIONS | | CON-VERSION, |
|---|---|---|---|---|---|---|---|---|
| EXAMPLE | Flow Rate ml/min. | g, moles | Conc. vol. % | Temp. °C. | Flow Rate ml/min. | Temp. °C. | Time Hours | %[2] |
| 16 | 7.67 | 1.5, 0.082 | 1.1 | 80 | 98.0 | 175 | 4.0 | 41.0 |
| 17 | 6.84 | 1.3, 0.072 | 0.9 | " | " | " | " | 49.8 |
| 18 | 10.62 | 2.6, 0.14 | 1.5 | " | " | " | 5.0 | 77.6 |
| 19 | 7.70 | 1.3, 0.072 | 1.0 | " | " | " | 3.5 | 81.1 |
| 20 | 4.77 | 0.9, 0.050 | 0.7 | " | " | " | 4.1 | 96.4 |
| 21 | 12.33 | 2.1, 0.12 | 1.7 | " | " | " | 3.6 | 88.5 |
| 22 | 20.12 | 5.8, 0.32 | 2.7 | " | " | " | 6.0 | 66.4 |
| 23 | 16.55 | 4.0, 0.22 | 2.2 | " | " | " | 5.0 | 85.0 |
| 24 | 15.94 | 4.6, 0.26 | 2.3 | " | " | " | 6.0 | 93.4 |
| 25 | 3.13 | 0.8, 0.044 | 0.4 | 85 | " | 180 | 5.5 | 99.7 |
| 26 | 0.14 | 0.04, 0.0022 | 0.02 | " | " | " | 6.0 | 78.4 |
| 27 | 24.31 | 5.9, 0.33 | 3.5 | " | " | " | 5.0 | 67.7 |
| 28 | 17.61 | 4.7, 0.26 | 1.6 | " | " | " | 5.5 | 22.1 |
| 29 | 18.29 | 5.3, 0.29 | 2.3 | " | " | " | 6.0 | 36.1 |
| 30 | 27.86 | 8.1, 0.45 | 4.0 | " | " | " | " | 71.9 |
| 31 | 34.80 | 8.4, 0.47 | 4.8 | " | " | " | 5.0 | 88.1 |
| 32 | 38.00 | 4.6, 0.26 | 4.3 | " | " | 160 | 2.5 | 66.8 |
| 33 | 23.02 | 2.2, 0.12 | 2.6 | " | " | " | 2.0 | 83.1 |
| 34 | 16.53 | 5.6, 0.31 | 2.3 | " | " | 175 | 7.0 | 1.8 |

TABLE 2-continued

| | | | | | | | | |
|---|---|---|---|---|---|---|---|---|
| 35 | 16.80 | 4.8, 0.27 | 2.3 | " | " | " | 6.0 | 49.8 |
| 36 | 16.80 | 4.9, 0.27 | 2.3 | " | " | " | " | 44.3 |
| 37 | 28.26 | 9.5, 0.53 | 4.0 | " | " | " | 7.0 | 51.7 |
| 38 | 12.86 | 3.1, 0.17 | 1.8 | " | " | " | 5.0 | 67.1 |
| 39 | 15.76 | 3.8, 0.21 | 2.2 | " | " | " | " | 74.2 |
| 40 | 14.93 | 4.3, 0.24 | 2.1 | " | " | " | 6.0 | 93.6 |
| 41 | 21.16 | 5.1, 0.28 | 2.9 | 80 | " | " | 5.0 | 90.9 |
| 42 | 15.73 | 11.6, 0.64 | 2.2 | " | " | " | 6.0 | 77.7 |
| 43 | 11.85 | 4.0, 0.22 | 1.7 | " | " | 180 | 7.0 | 86.9 |
| 44 | 7.81 | 2.3, 0.13 | 1.1 | " | " | 190 | 6.0 | 86.5 |
| 45 | 6.26 | 1.8, 0.10 | 0.9 | " | " | 185 | " | 70.2 |
| 46 | 25.12 | 6.7, 0.37 | 3.3 | 88 | 135.0 | 175 | 5.5 | 5.3 |
| 47 | 26.13 | 6.3, 0.35 | 3.4 | " | " | " | 5.0 | 52.4 |
| 48 | 22.97 | 7.2, 0.40 | 3.0 | " | " | " | 6.5 | 60.1 |
| 49 | 14.80 | 4.2, 0.23 | 2.0 | " | " | " | 5.8 | 3.0 |
| 50 | 16.43 | 4.0, 0.22 | 3.2 | " | 105.0 | " | 5.0 | 77.0 |
| 51 | 8.21 | 2.0, 0.11 | 1.1 | 85 | 98.0 | " | " | 35.6 |
| 52 | 19.91 | 4.3, 0.24 | 2.6 | 88 | 135.0 | " | 4.5 | 93.3 |
| 53 | 20.53 | 5.9, 0.33 | 2.7 | " | " | " | 6.0 | 77.2 |
| 54 | 24.27 | 7.0, 0.39 | 3.2 | " | " | " | " | 73.7 |
| 55 | 20.36 | 5.4, 0.30 | 2.7 | " | " | " | 5.5 | 81.9 |
| 56 | 23.02 | 6.6, 0.37 | 3.0 | " | " | " | 6.0 | 44.8 |
| 57 | 16.43 | 4.0, 0.22 | 3.3 | " | 105.0 | " | 5.0 | 88.8 |
| 58 | 22.40 | 6.0, 0.33 | 2.9 | " | 135.0 | " | 5.5 | 8.3 |
| 59 | 21.65 | 5.3, 0.29 | 2.8 | " | " | " | 5.0 | 94.3 |
| 60 | 8.89 | 1.5, 0.083 | 1.2 | 80 | 98.0 | " | " | 4.3 |
| 61 | 6.91 | 1.5, 0.083 | 1.0 | " | " | " | 4.5 | 63.1 |
| 62 | 20.48 | 5.0, 0.28 | 3.6 | 40 | 405 | 155 | 5.0 | 65.9 |
| 63[12] | 25.80 | 6.2, 0.34 | 4.1 | 50 | " | " | " | 99.1 |
| 64 | 23.85 | 5.8, 0.32 | 4.2 | 40 | " | 154 | " | 84.6 |
| 65[12] | 19.41 | 4.7, 0.26 | 3.3 | " | " | 155 | " | 99.4 |
| 66 | 23.89 | 5.8, 0.32 | 4.2 | " | " | " | " | 90.0 |
| 67 | 30.95 | 7.5, 0.42 | 5.6 | 50 | " | 154 | " | 61.9 |
| 68 | 23.57 | 6.2, 0.34 | 4.2 | 40 | " | 134 | 5.5 | 78.7 |
| 69 | 14.31 | 2.8, 0.16 | 2.7 | 41 | " | 174 | 4.0 | 24.8 |
| 70 | 19.08 | 4.6, 0.26 | 3.7 | " | " | 154 | 5.0 | 11.5 |
| 71 | 23.44 | 5.6, 0.31 | 3.3 | " | 580 | 177 | " | 36.4 |
| 72 | 17.92 | 4.3, 0.24 | 2.4 | 40 | " | 172 | " | 48.7 |
| 73 | 23.91 | 5.4, 0.30 | 4.2 | " | 405 | 232 | 4.7 | 12.7 |
| 74 | 42.23 | 10.2, 0.57 | 3.8 | 34.5 | 940 | 192 | 5.0 | 27.6 |

| | PRODUCTS, % | | | | | | MATERIAL BALANCE | | |
|---|---|---|---|---|---|---|---|---|---|
| | | R—C$_6$H$_4$—NO$_2$ | | | | | | g | |
| | | R = CH$_3$, C$_2$H$_5$O, Cl | | | | | | | |
| EXAMPLE | R = H | ortho | meta | para | Unidentified by- | para/ortho | In | Out | % |
| 16 | — | 9.8 | 0.9 | 30.3 | — | 3.09 | 55.4 | 46.4 | 83.8 |
| 17 | — | 13.8 | 1.0 | 34.4 | — | 2.49 | 63.8 | 62.8 | 98.4 |
| 18 | — | 20.3 | 1.6 | 55.5 | 0.2 | 2.73 | 78.6 | 68.6 | 87.3 |
| 19 | — | 22.2 | 1.2 | 57.7 | — | 2.60 | 59.8 | 57.2 | 95.7 |
| 20 | — | 24.6 | 1.4 | 70.4 | — | 2.86 | 36.5 | 31.0 | 84.9 |
| 21 | — | 23.2 | 1.4 | 63.9 | <0.1 | 2.75 | 49.6 | 45.0 | 90.7 |
| 22 | — | 16.7 | 1.1 | 48.6 | <0.1 | 2.91 | 100.6 | 97.2 | 96.6 |
| 23 | — | 24.3 | 1.7 | 59.0 | — | 2.43 | 86.3 | 81.6 | 94.6 |
| 24 | — | 28.1 | 1.8 | 63.6 | — | 2.26 | 70.3 | 70.6 | 100.4 |
| 25 | — | 28.6 | 1.6 | 69.5 | <0.1 | 2.43 | 79.7 | 74.4 | 93.4 |
| 26 | — | 22.9 | 1.3 | 53.5 | 0.8 | 2.34 | 68.3 | 58.3 | 85.4 |
| 27 | — | 20.1 | 0.8 | 46.4 | 0.4 | 2.31 | 53.6 | 44.2 | 82.5 |
| 28 | — | 6.4 | 0.4 | 15.0 | 0.4 | 2.34 | 147.7 | 136.3 | 92.3 |
| 29 | — | 10.5 | 0.5 | 24.8 | 0.4 | 2.36 | 100.2 | 90.9 | 90.7 |
| 30 | — | 19.6 | 1.0 | 51.2 | 0.2 | 2.61 | 78.8 | 75.0 | 95.2 |
| 31 | — | 26.2 | 1.3 | 60.6 | 0.1 | 2.31 | 69.8 | 68.7 | 98.4 |
| 32 | 66.3 | — | — | — | 0.5 | — | 83.7 | 79.1 | 94.5 |
| 33 | 82.2 | — | — | — | 0.9 | — | 67.7 | 66.7 | 98.5 |
| 34 | — | 0.6 | — | 1.2 | — | 2.00 | 114.5 | 114.8 | 100.3 |
| 35 | — | 13.3 | — | 36.5 | — | 2.74 | 98.0 | — | — |
| 36 | — | 13.3 | — | 31.1 | — | 2.34 | 95.4 | 95.9 | 100.5 |
| 37 | — | 14.8 | 0.6 | 35.1 | — | 2.37 | 72.6 | 67.5 | 93.0 |
| 38 | — | 21.6 | 1.4 | 44.2 | — | 2.05 | 84.5 | 64.4 | 76.2 |
| 39 | — | 25.8 | 2.4 | 46.0 | — | 1.78 | 79.1 | 75.0 | 94.8 |
| 40 | — | 30.2 | 1.9 | 61.4 | — | 2.03 | 61.3 | 57.9 | 94.5 |
| 41 | — | 24.1 | 1.6 | 65.2 | — | 2.71 | 75.5 | 56.9 | 75.4 |
| 42 | — | 24.0 | 1.2 | 52.5 | — | 2.19 | 107.4 | 96.4 | 89.8 |
| 43 | — | 25.8 | 1.4 | 59.6 | — | 2.31 | 97.9 | 86.3 | 88.2 |
| 44 | — | 24.1 | 1.3 | 61.0 | — | 2.53 | 64.9 | 50.1 | 77.2 |
| 45 | — | 20.0 | 1.1 | 49.2 | — | 2.46 | 72.2 | 71.1 | 98.5 |
| 46 | — | 11.4 | 0.2 | 3.7 | — | 2.64 | 86.9 | 87.3 | 100.5 |
| 47 | — | 12.7 | 0.3 | 39.3 | — | 3.09 | 76.4 | 67.4 | 88.2 |
| 48 | — | 14.6 | 0.1 | 45.3 | — | 3.10 | 95.6 | 87.9 | 91.9 |
| 49 | — | 0.8 | 0.1 | 2.0 | — | 2.50 | 77.5 | 79.4 | 102.5 |
| 50 | — | 17.8 | 0.1 | 49.0 | — | 2.75 | 42.1 | 38.3 | 91.0 |

TABLE 2-continued

| | | | | | | | | | |
|---|---|---|---|---|---|---|---|---|---|
| 51 | — | 10.4 | 0.3 | 24.9 | — | 2.39 | 72.3 | 69.6 | 96.3 |
| 52 | — | 18.9 | 1.1 | 63.4 | — | 3.35 | 68.7 | 69.0 | 100.4 |
| 53 | — | 16.8 | 1.1 | 59.3 | — | 3.53 | 86.8 | 86.8 | 100.0 |
| 54 | — | 16.3 | 0.9 | 56.5 | — | 3.47 | 86.4 | 88.0 | 101.9 |
| 55 | — | 18.2 | 1.1 | 62.7 | — | 3.45 | 76.8 | 78.0 | 101.6 |
| 56 | — | 12.6 | 0.2 | 32.0 | — | 2.54 | 83.2 | 76.6 | 92.1 |
| 57 | — | 26.7 | 1.0 | 61.1 | — | 2.29 | 38.4 | 35.9 | 93.5 |
| 58 | — | 2.3 | 0.1 | 5.8 | — | 2.52 | 82.1 | 83.1 | 101.2 |
| 59 | — | 26.8 | 0.7 | 66.7 | <0.1 | 2.49 | 72.7 | 69.7 | 95.9 |
| 60 | — | 0.4 | 0.2 | 0.8 | 3.0 | 2.00 | 55.0 | 52.6 | 95.6 |
| 61 | — | 14.6 | 1.0 | 47.6 | — | 3.26 | 67.3 | 64.1 | 95.2 |
| 62 | 65.9 | — | — | — | — | — | 103.1 | 101.6 | 98.5 |
| 63[12] | 99.1 | — | — | — | — | — | 123.2 | 117.0 | 95.0 |
| 64 | 84.6 | — | — | — | — | — | 91.8 | 91.4 | 99.6 |
| 65[12] | 99.4 | — | — | — | — | — | 99.9 | 95.1 | 95.2 |
| 66 | 90.4 | — | — | — | — | — | 95.0 | 93.4 | 98.3 |
| 67 | 61.9 | — | — | — | — | — | 76.1 | 70.3 | 92.4 |
| 68 | 78.7 | — | — | — | — | — | 100.3 | 98.8 | 98.5 |
| 69 | — | 13.7 | — | 11.1 | — | 0.81 | 62.0 | 56.5 | 91.1 |
| 70 | — | 6.0 | — | 5.5 | — | 0.92 | 68.8 | 59.4 | 86.3 |
| 71 | — | 17.2 | — | 19.2 | — | 1.12 | 73.6 | 70.5 | 95.8 |
| 72 | — | 23.3 | — | 25.2 | 0.2 | 1.09 | 82.7 | 72.4 | 87.5 |
| 73 | — | 1.5 | 0.1 | 11.1 | — | 7.40 | 101.9 | 69.9 | 68.6 |
| 74 | — | 6.3 | — | 21.3 | — | 3.38 | 97.1 | 75.4 | 77.7 |

[1]Nitrogen dioxide (M.W., 46) unless specified otherwise.
[2]Based on the aromatic compound.
[3]Air
[4]Nitrogen
[5]Numbered catalyst precursor prior to treatment for sulfur trioxide uptake. Comparative run to demonstrate the effectiveness of the present invention over prior art catalysts.
[6]Pretreated catalyst for 15 minutes with nitrogen dioxide at operating conditions (for the vapor phase nitration in the absence of the aromatic compound).
[7]Pretreated catalyst as described in Footnote 6 for 12 minutes.
[8]Pretreated catalyst as described in Footnote 6 for 10 minutes.
[9]Pretreated catalyst as described in Footnote 6 for 3 minutes.
[10]No pretreatment.
[11]Catalyst 14 was employed as the catalyst in Examples 62-72 without further treatment with sulfur dioxide and nitrogen dioxide.
[12]Reaction was run at a gauge pressure of $1.03 \times 10^5$ pascal (Pa; 15 psig).
[13]Catalyst 15 was employed as the catalyst in Examples 73-74 without further treatment with sulfur dioxide and nitrogen dioxide.

EXAMPLE 75-78

The following examples were run to illustrate the use of the catalyst compositions of the present invention as catalysts in the vapor phase nitration of disubstituted aromatic compounds using o- or 1,2-dichlorobenzene as a typical compound.

The reactor system described in Examples 1-15 and the procedure described in Examples 16-74 were employed. The parameters and results are tabulated in Table 3.

TABLE 3

| | | AROMATIC COMPOUND, R—$C_6H_4$—$R^1$ | | | | | | |
|---|---|---|---|---|---|---|---|---|
| EXAMPLE | CATALYST NUMBER | R | $R^1$ | Flow Rate ml/min. | g, moles | Conc. vol. % | Temp. °C. | Carrier Gas[3] Flow Rate ml/min. |
| 75 | 14[5] | 1-Cl | 2-Cl | 46.11 | 90.8, 0.62 | 8.1 | 21 | — |
| 76 | 14 | " | " | 40.51 | 79.7, 0.54 | 7.4 | " | — |
| 77 | 14 | " | " | 43.48 | 85.6, 0.58 | 7.1 | " | — |
| 78 | 14 | " | " | 43.26 | 85.2, 0.58 | 5.6 | " | — |

| | NITRATING AGENT[1] | | | | | NITRATING AGENT/- AROMATIC COMPOUND |
|---|---|---|---|---|---|---|
| EXAMPLE | Flow Rate ml/min. | g, moles | Conc. vol. % | Temp. °C. | Carrier Gas[4] Flow Rate ml/min. | molar ratio |
| 75 | 64.57 | 39.8, 0.87 | 11.3 | 10 | 36.5 | 1.40 |
| 76 | 49.23 | 30.3, 0.66 | 9.0 | " | " | 1.22 |
| 77 | 102.42 | 63.1, 1.37 | 16.6 | " | 45.0 | 2.36 |
| 78 | 99.21 | 61.1, 1.33 | 12.5 | " | " | 2.29 |

| | WATER | | | | | REACTION CONDITIONS | | |
|---|---|---|---|---|---|---|---|---|
| EXAMPLE | Flow Rate ml/min. | g, moles | Conc. vol. % | Temp. °C. | Carrier Gas[3] Flow Rate ml/min. | Temp. °C. | Time Hours | CONVER- SION, %[2] |
| 75 | 20.16 | 4.9, 0127 | 3.5 | 41 | 405 | 175 | 5.0 | 1.1 |
| 76 | 17.17 | 4.1, 0.23 | 3.1 | 40 | " | 206 | " | 3.0 |
| 77 | 20.78 | 5.0, 0.28 | 3.4 | " | " | 255 | " | 16.2 |
| 78 | 33.27 | 8.0, 0.44 | 4.2 | " | 570 | 281 | " | 29.3 |

PRODUCTS, %

TABLE 3-continued

| | R—C$_6$H$_3$—NO$_2$— R$^1$ R = R$^1$ = Cl | | | | MATERIAL BALANCE g | | |
|---|---|---|---|---|---|---|---|
| EXAMPLE | 2,3- | 3,4- | By- | 3,4/2,3- | In | Out | % |
| 75 | 0.05 | 0.5 | 0.55 | 10.00 | 135.5 | 123.9 | 91.4 |
| 76 | 0.4 | 2.0 | 0.6 | 5.00 | 114.1 | 110.7 | 97.0 |
| 77 | 2.6 | 11.8 | 1.8 | 4.54 | 153.7 | 146.1 | 95.1 |
| 78 | 3.5 | 19.6 | 6.2 | 5.60 | 154.3 | 148.6 | 96.3 |

[1]Nitrogen dioxide (M.W., 46) unless specified otherwise.
[2]Based on the aromatic compound.
[3]Air
[4]Nitrogen
[5]Catalyst 14 after being employed as the catalyst in Examples 62-72 above, was employed in Examples 75-78 without further treatment with sulfur dioxide and nitrogen dioxide.

Thus, it is apparent that there has been provided in accordance with the present invention, catalysts and a process for preparing same that fully satisfy the objects and advantages set forth hereinabove. While the invention has been described with respect to various specific examples and embodiments thereof it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A catalyst composition comprising the adduct of:
   (a) an alumina-metal oxide combination represented by the formula $(Al_2O_3)_a(M_{2/n}O)_c$ wherein M is a metal cation selected from the group consisting of the lanthanides, Groups 1b, 2b, 5b, 6b, 7b, and 8 of the Periodic Table of the Elements, and mixtures thereof, and a and c represent weight percent of the Al$_2$O$_3$ and M$_{2/n}$O components, respectively, in the alumina-metal oxide combination, with a being 50 to 100 and c being 0 to 50, and n is an integer from 1 to 7 of the valence of the metal cation, and
   (b) a catalytically effective amount of sulfur trioxide.

2. The catalyst composition of claim 1 wherein the amount of sulfur trioxide is in the range from about 5 weight percent to about 40 weight percent, based on the weight of the alumina-metal oxide combination.

3. The catalyst composition of claim 1 wherein the alumina-metal oxide combination is selected from the group consisting of crystalline and noncrystalline phases, and mixtures thereof.

4. The catalyst composition of claim 1 wherein a is 100, and c is 0.

5. The catalyst composition of claim 1 wherein M is a mixture of metal cations.

6. The catalyst composition of claim 5 wherein M is a mixture of cobalt and molybdenum, with n being, respectively, 2 and 6.

7. The catalyst composition of claim 6 wherein a is 86.5 and c is 13.5.

8. The catalyst composition of claim 7 wherein c comprises 3.5 weight percent cobalt (II) oxide and 10 weight percent molybdenum (VI) oxide.

9. The catalyst composition of claim 7 wherein a is 80.5 and c is 19.5.

10. The catalyst composition of claim 9 wherein c comprises 4.5 weight percent cobalt (II) oxide and 15 weight percent molybdenum (VI) oxide.

11. A process for preparing a catalyst composition which comprises contacting an alumina-metal oxide combination represented by the formula $(Al_2O_3)_a(M_{2/n}O)_c$ wherein M is a metal cation selected from the group consisting of the lanthanides, Groups 1b, 2b, 5b, 6b, 7b, and 8 of the Periodic Table of the Elements, and mixtures thereof, and a and c represent weight percent of the Al$_2$O$_3$ and M$_{2/n}$O components, respectively, in the alumina-metal oxide combination, with a being 50 to 100 and c being 0 to 50, and n is an integer from 1 to 7 of the valence of the metal cation, with a catalytically effective amount of gaseous sulfur trioxide.

12. The process of claim 11 wherein the effective amount of sulfur trioxide is in the range from about 5 weight percent to about 40 weight percent, based on the weight of the alumina-metal oxide combination.

13. The process of claim 11 wherein the contacting of the alumina-metal oxide combination with the sulfur trioxide is carried out under substantially anhydrous conditions at a temperature from about 25° C. to about 300° C.

14. The process of claim 13 wherein the temperature is from about 150° C. to about 225° C.

15. The process of claim 14 wherein the temperature is about 175° C.

16. The process of claim 11 wherein the sulfur trioxide is provided by contacting the alumina-metal oxide combination with a mixture of sulfur dioxide and nitrogen dioxide.

17. The process of claim 16 wherein the mole ratio of sulfur dioxide to nitrogen dioxide is at least 1.

18. The process of claim 17 wherein the mole ratio of sulfur dioxide to nitrogen dioxide is about 2-3/1.

19. The process of claim 11 wherein a is 100, and b and c each is 0.

20. The process of claim 11 wherein M is a mixture of metal cations.

21. The process of claim 20 wherein M is a mixture of cobalt and molybdenum, with n being, respectively, 2 and 6.

22. The process of claim 21 wherein a is 86.5 and c is 13.5.

23. The process of claim 22 wherein c comprises 3.5 weight percent cobalt (II) oxide and 10 weight percent molybdenum (VI) oxide.

24. The process of claim 21 wherein a is 80.5 and c is 19.5.

25. The process of claim 24 wherein c comprises 4.5 weight percent cobalt (II) oxide and 15 weight percent molybdenum (VI) oxide.

* * * * *